United States Patent [19]
Rens et al.

[11] Patent Number: 5,985,216
[45] Date of Patent: Nov. 16, 1999

[54] FLOW CYTOMETRY NOZZLE FOR HIGH EFFICIENCY CELL SORTING

[75] Inventors: Willem Rens, Norfolk, United Kingdom; Glenn R. Welch; Lawrence A. Johnson, both of Silver Spring, Md.

[73] Assignee: The United States of America, as represented by the Secretary of Agriculture, D.C., Wash.

[21] Appl. No.: 08/898,999

[22] Filed: Jul. 24, 1997

[51] Int. Cl.[6] .................................................. G01N 33/48
[52] U.S. Cl. .............................. 422/73; 422/81; 422/99; 422/100; 356/23; 356/246; 356/336; 239/423
[58] Field of Search .................................. 422/73, 81, 99, 422/100; 356/23, 246, 336, 337; 239/423, 424

[56] References Cited

U.S. PATENT DOCUMENTS

| | | | |
|---|---|---|---|
| 3,893,766 | 7/1975 | Hogg | 356/246 X |
| 4,361,400 | 11/1982 | Gray et al. | 356/23 |
| 4,983,038 | 1/1991 | Ohki et al. | 356/246 |
| 4,988,619 | 1/1991 | Pinkel | 435/30 |
| 5,007,732 | 4/1991 | Ohki et al. | 356/73 |
| 5,199,040 | 3/1993 | Kuklo | 356/246 X |
| 5,311,290 | 5/1994 | Olson et al. | 356/246 X |
| 5,412,466 | 5/1995 | Ogino | 356/246 |
| 5,690,895 | 11/1997 | Matsumoto et al. | 422/73 |

OTHER PUBLICATIONS

Kachel, V., "Uniform Lateral Orientation, Caused by Flow Forces, of Flat Particles in Flow–Through Systems", *The Journal of Histochemistry and Cystochemistry*, vol. 25, No. 7, pp. 774–780, 1977.
P.N. Dean et al. *Biophys J.* 1978, 23, 7–13.
R.T. Stovel et al. *Biophys. J.* 1978, 23, 1–5.
D. Pinkel et al. *Cytometry* 1982, 3, 1–9.
B.L. Gledhill et al. *J. Cell. Physiol.* 1976, 87, 367–375.
W. Rens et al. *Cytometry* 1994, 16, 8–87.
W. Rens et al. *Cytometry* 1996, 25, 191–199.

*Primary Examiner*—Arlen Soderquist
*Attorney, Agent, or Firm*—M. Howard Silverstein; Curtis P. Ribando; John D. Fado

[57] ABSTRACT

A sorting nozzle having two tapered zones with elliptical cross-sections is able to orient and sort a large fraction of asymmetrical or "flattened" cells. This nozzle has particular application for sorting viable male (Y) and female (X) sperm populations in a cell sorter.

7 Claims, 3 Drawing Sheets

FLOW CYTOMETRY NOZZLE FOR HIGH EFFICIENCY CELL SORTING

BACKGROUND OF THE INVENTION

1. Field of the Invention

The physical separation of semen into purified X- and Y-chromosome bearing sperm populations using flow cytometry and sorting has proven to be effective in humans, cattle, swine, sheep and rabbits for gender preselection.

The success of the sorting process is dependent on the accuracy and efficiency of analyzing sperm for DNA content. High resolution flow cytometric DNA analysis of sperm is hampered by its uneven emission of fluorescence. Due to the sperm head's flat shape, compactness of chromatin and a high index of refraction, fluorescence from the edge is much brighter than from the flat side of the sperm (Gledhill et al., *J Cell Physiol.* 87:367–376 (1976); Johnson et al., *Cytometry* 7:268–273 (1986); and Pinkel et al., *Cytometry* 3:1–9 (1982)]. This fact, coupled with random orientation, results in a broad fluorescence distribution hiding specific subpopulations with different contents of DNA within a sample. A solution for this problem is to use an epiillumination flow cytometer employing co-axial flow characteristics. However, this system is generally not suitable for cell sorting. The only solution that incorporates DNA analysis and sorting is to collect only fluorescence from properly oriented cells using an orthogonal flow cytometer/cell sorter (Johnson et al. and Pinkel et al., supra). In the orthogonal system, a 90° fluorescence detector is used for detection of properly oriented sperm. A bright signal indicates that a sperm's bright edge is effectively orientated to the 90° detector and consequently the flat side will face the laser beam. A forward fluorescence detector (0°) is added to the cell sorter to collect the fluorescence from the flat face opposite to the laser beam. The forward fluorescence signal when collected from the flat side of the properly orientated sperm is an accurate measurement of DNA content (Johnson et al. and Pinkel et al., supra).

Improved high efficiency sorting can only be valuable for sperm sexing if three criteria are met:

1) It does not decrease the accuracy of the DNA measurement (maintain 90% purities).
2) Stability of sort is not compromised (time not wasted adjusting cell sorter).
3) Enough sperm can be recovered enabling their use for in vitro fertilization and artificial insemination.

This invention relates to a novel nozzle which is designed to orient and sort a large fraction of sperm independent of sheath fluid velocity and sample rate.

2. Description of the Prior Art

The orientation of sperm (cells) is random in conventional cell sorters. For sperm sexing, cell sorters have been modified by replacing the sample injection needle with a beveled needle [Dean et al., *Biophys. J.* 23:7–13 (1978); Fulwyer, *J. Histochem. Cytochem.* 25:781–783 (1977); Johnson et al., supra; Pinkel et al., supra; Stovel, et al., *Biophys. J.* 23:1–5 (1978); and Welch et al., *Cytometry* 17(Suppl. 7): 74 (1994)]. This beveled needle forces a larger proportion of sperm to pass the laser beam in the proper orientation because it reshapes the cylindrical sample stream into a thin ribbon. The beveled needle helps to orient sperm, especially sperm heads, e.g., sperm without their tail. The sample core leaving the beveled needle will be in the shape of a ribbon, which applies orienting forces to the sperm. However this ribbon only exists when the sample stream is narrow; that is, under low sample pressure and concomitant low sample rate. These conditions are not advantageous for efficient sperm sorting. Also, the improvement in orientation attributed to use of a beveled needle is less pronounced for living and motile sperm. Only 20–40% of intact viable sperm are correctly orientated using this system [Johnson, *Reprod. Fertil. Dev.* 7:893–903 (1995)]. This means that between 60% and 80% of the detected sperm are not analyzed for DNA analysis. The ability to sort intact and viable cells in conjunction with improved orientation efficiency would lead to a much higher sorting efficiency.

Kachel et al. [*J. Histochem. Cytochem.* 25:774–780 (1977)] disclose an asymmetric Plexiglas® chamber for orienting flat particles (fixed chicken erythrocytes) on a microscope. Kachel et al. suggest that the simplest flow path for applying the necessary hydrodynamic focusing forces consists of a tube with an elliptical cross-section and ending in an elliptical outlet having a long axis at right angles to the long axis in the cross-section of the constricting elliptical tube. This device was not proposed for use in combination with a cell sorter.

SUMMARY OF THE INVENTION

We have now discovered a novel nozzle design useful specifically for high efficiency flow sorting of asymmetrical or "flattened" cells in a cell sorter. The nozzle's unique design incorporates two ellipsoidal interior zones and an elliptical exit orifice capable of stable droplet formation and cell sorting. A unique performance characteristic of the nozzle of the invention is that, when used with intact viable sperm, the proportion of oriented sperm are essentially independent of sperm motility, sample rate, and sheath stream velocity.

In accordance with this discovery, it is an object of the invention to provide a cell sorter nozzle that will improve the efficiency of correctly orienting nonradially symmetrical cells in a separation stream.

It is a specific object of the invention to provide a means for improving the accuracy and efficiency of sperm cell sorting in a flow cytometer.

It is another object of the invention to enable the utilization of high speed cell sorters in order to maximize the number of sorted sperm per unit time.

Other objects and advantages of the invention will become readily apparent from the ensuing description.

DETAILED DESCRIPTION OF THE INVENTION

The novel nozzle design of the invention is most typically embodied as a stream jet-in-air nozzle which is described in the ensuing discussion. However, it would be appreciated by a person of ordinary skill in the art that the design could be incorporated into other types of nozzles as well, such as a quartz channel nozzle.

Figure 1:
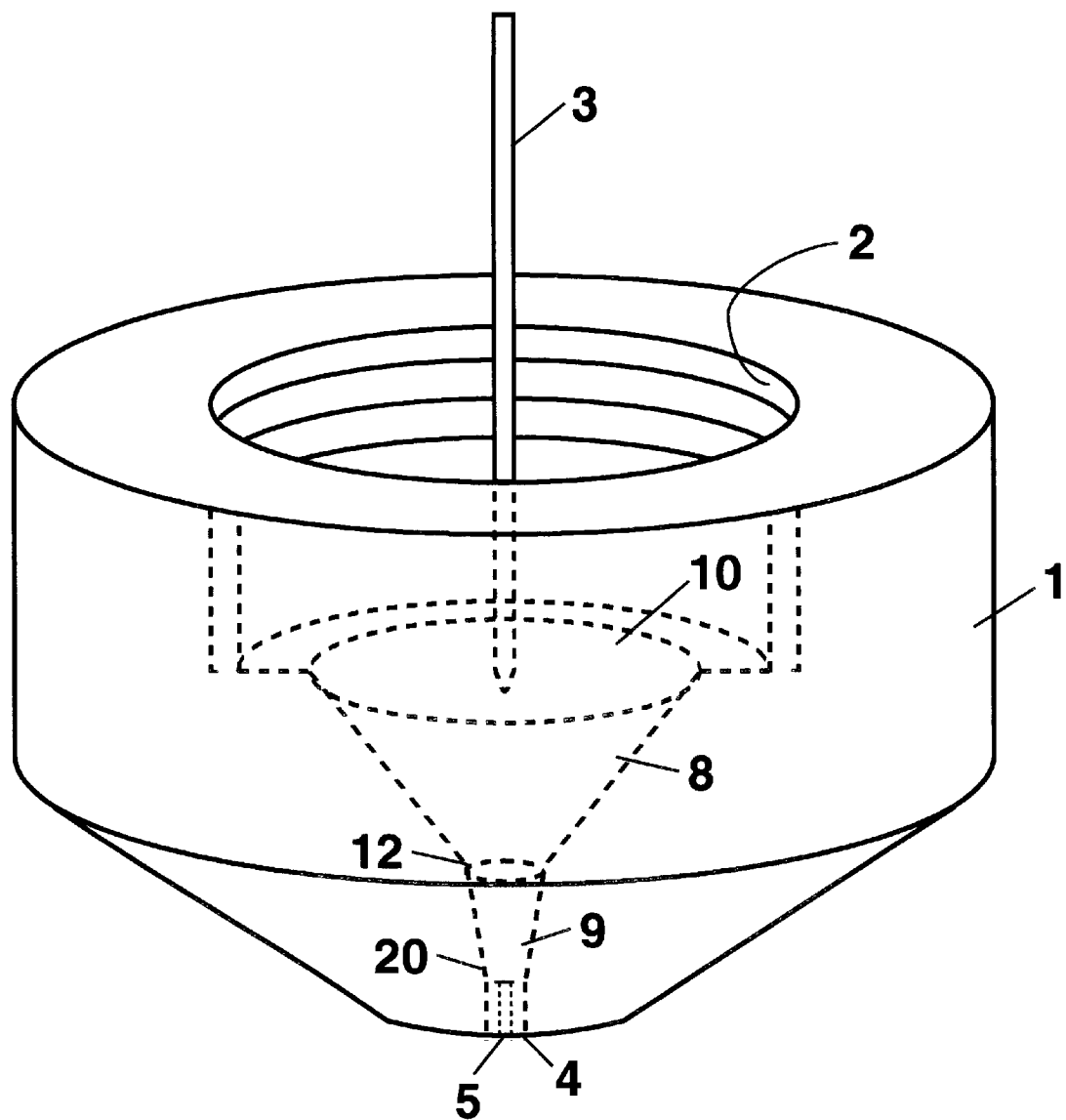
FIG. 1 is a perspective view of one embodiment of the nozzle of the invention.
Figure 2A:
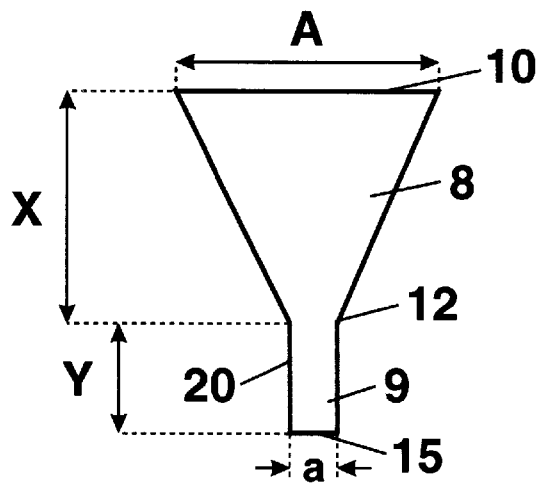
FIG. 2A is a front elevation interior outline of the nozzle of the invention.
Figure 3A:
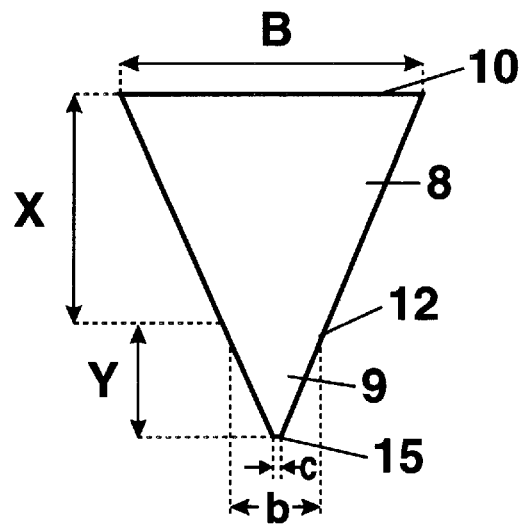
FIG. 3A is a side elevation interior outline of the nozzle of the invention.
Figure 2B:
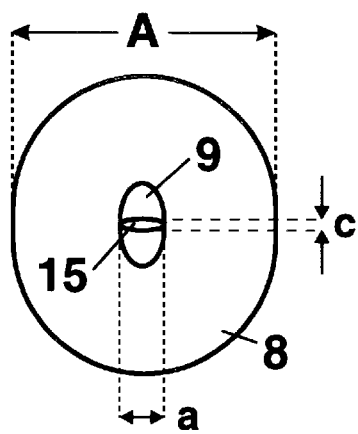
FIG. 2B is a top view of the interior outline of the nozzle as depicted in FIG. 2A.
Figure 3B:
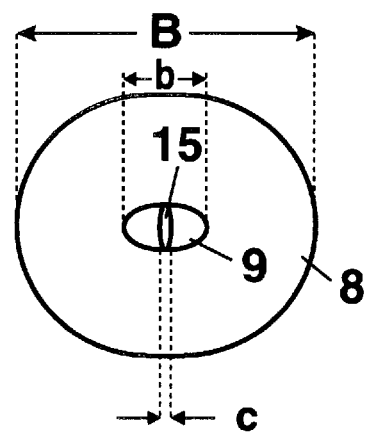
FIG. 3B is a top view of the interior outline of the nozzle as depicted in FIG. 3A.

Referring to FIG. 1, the nozzle essentially comprises a body 1 having interior threads 2 or other suitable means for attachment to the flow cell body or nozzle holder (not shown). In an alternate embodiment, a pressure fitting could be used instead of mating threads for attaching the nozzle to the holder. The interior of the nozzle is adapted to receive sample injection needle 3, which is adjusted to extend into the nozzle a sufficient depth to maintain laminar flow. The injection needle may be a standard cylindrical needle or it may be beveled. In the tip of the nozzle, opposite the means for attachment, is a cylindrical orifice 5 which serves as the final exit from the flow nozzle. Orifice 5 is typically drilled into a jewel 4 which is positioned at the end of nozzle body 1.

Referring to FIGS. 2A, 2B, 3A and 3B, the interior of the nozzle comprises a first ellipsoidal zone 8 and a second ellipsoidal zone 9 separated by a transition zone 12. Virtually all cross-sections of the first and second zones and of the transition zone 12 are each in the shape of an ellipse having a long axis and a short axis. The first zone 8 is tapered from the mouth to the transition zone such that the cross-sectional area of said transition zone is less than that of the mouth. The second zone is tapered from the transition zone to an exit orifice 15 having a cross-sectional area less than that of the transition zone. The long axis of the exit orifice ellipse is oriented approximately 90° to the long axes of both the mouth and the transition zone. Orifice 5 is immediately downstream from the elliptical exit orifice 15. Orifice 5 is concentrically aligned with exit orifice 15 and also has a smaller cross-sectional area than the exit orifice. The interior shape of nozzle 1 can be visualized with a standard flexible funnel by compressing opposite sides of the bowl of the funnel to form an oval shape at the mouth, and by compressing the stem of the funnel at 90° to the compressive forces applied to the bowl to form an elliptical slit at the stem outlet.

The actual and relative dimensions of the nozzle interior in a preferred embodiment of the invention are given in Table I, below. The dimension references are found in FIGS. 2A, 2B, 3A, and 3B. Dimensions A and p represent the short and the long axes, respectively, of mouth 10. Dimensions a and b represent the short and the long axes, respectively, of transition zone 12. Dimension a also represents the long axis of exit orifice 15. Dimension c represents the short axis of the orifice. Dimension X is the height of first zone 8 and Y is the height of second zone 9. The dimensions given in Table I are considered to be approximately optimal for the purpose of orienting viable intact sperm. However, it would be appreciated by the person in the art, that these dimensions could be varied within reasonable limits without significantly altering the functional ability of the nozzle to sort while orienting viable sperm or other asymmetrical cells or objects. The tolerances for these dimensions are at least about ∓10% of the values given in Table I.

Table II presents ratios of various significant nozzle dimensions based upon the relationships given in Table I. These ratios may vary within limits of ∓20%, with the proviso that the ratio of B/A remains greater than 1 so that mouth 10 is elliptical. Typically, the ratio of B/A should be at least about 1.1. In comparing the ratio B/A to the ratio b/a, it is apparent that the relative dimensions of the long axis to the short axis of cross-sections of the first zone progressively increase from the mouth of the zone to the transition zone.

In succeeding cross-sections downstream from the transition zone, that is, in the second zone, the long axis/short axis ratio begins to decline. At an "inversion" point 20 which is intermediate transition zone 12 and exit orifice 15, the axes are equal and the interior cross-section of the second zone is circular. From the inversion point to the exit orifice, cross-sections of the second zone are again elliptical; but the long axes of the cross-sections are at 90° to the long axes of the cross-sections above the inversion point. For the ellipses inscribed by each succeeding cross-section approaching the exit orifice, the ratios of the long axes to the short axes progressively increase. It is understood that in each progressively downstream cross-section from the mouth of the nozzle to the exit office, the dimensions of both the long axis and the short axis decrease commensurate with the continuous tapering of both the first and second zones.

The elliptical nozzle of this invention is capable of orienting in excess of 60% of sperm for sorting. When compared to a conventional system employing a standard cylindrical nozzle in combination with a standard conical sample injection needle wherein sperm traverse the laser beam with random orientation, the elliptical nozzle achieves approximately a three-fold increase in the proportion of sperm oriented for sorting. Approximately a two-fold increase in efficiency is obtained in comparison with a standard conical nozzle in combination with a beveled injection needle. When a beveled needle is used to orient sperm, the fraction of oriented sperm decreases with increasing sample rate. We have found that with the elliptical nozzle, the proportion of proper orientation is maintained at sample rates up to at least 15,000 sperm per second. This high level of performance is beneficial for efficient sperm sorting. In tests with bovine sperm (Example 5), it is apparent that a cell sorter equipped with the new nozzle effectively separates X- and Y-chromosome bearing sperm into sorting purities of approximately 90%.

The nozzle of the invention is envisioned to be useful for sorting viable sperm of any mammalian species as well as for sorting blood cells, seeds and other asymmetrical units. Tests with bovine sperm (Example 2) indicate that performance of the nozzle is not influenced by sperm motility.

A high speed sorter equipped with the nozzle of this invention increases the yield of sorted X- and Y-chromosome bearing sperm 10-fold and will make artificial insemination with sexed sperm a more feasible alternative to in vitro fertilization and embryo transfer or surgical insemination in gender preselection of livestock and other animals.

The following examples are intended to further illustrate the invention.

EXAMPLES

Sperm Preparation and Staining

Ejaculated semen from several mature bulls and boars of proven fertility and on regular collection schedules, and semen from mature New Zealand White bucks (rabbit) were used for this study. In addition, one semen sample each of the mouse and human was evaluated for demonstration purposes because of the differing head shapes of their sperm. Sperm preparation and staining were based on the method described by Johnson et al. [*Biol. Repro.* 41:199–203 (1989)] and Johnson et al. [*Gamete Research* 17:203–212 (1987)]. Briefly, aliquots of neat semen were extended to a concentration of $15-10^6$/ml to $100 \times 10^6$/ml in: Hepes buffered medium containing 0.1% BSA (pH=7.4) for bull sperm, Beltsville Thawing Solution (BTS, pH=7.2) for boar sperm, and Tris buffer (0.21 M Tris, 58 mM glucose, and 67 mM citric acid; pH=6.9) for rabbit sperm. Mouse and human semen were extended in BTS. Sperm were subsequently stained with 7.1 $\mu$M Hoechst 33342 per 15×10$^6$ sperm (Calbiochem-Behring Corp., La Jolla, Calif.) and incubated over a 40-min period at 32° C. For the bull sperm studies, just prior to analysis propidium iodide (PI) (1.5 $\mu$M, Calbiochem-Behring Corp., La Jolla, Calif.) was added to the Hoechst 33342 stained sperm. This allowed dead sperm to be distinguished from living sperm as described by Johnson et al. (1994, supra).

Cell Sorting

For Examples 1–5, two variations of a standard cell sorting system were used for sorting viable intact sperm with the nozzle of invention: the EPICS® V series flow cytometer/cell sorter (Coulter Corporation, Miami Fla.) and the EPICS® 750 (a modified version of the EPICS® V). For Examples 6 and 7, a newer system, the MoFlo® high speed cell sorter (Cytomation Inc., Fort Collins, Colo.) was used. Each cell sorter was modified for sorting sperm as described in Johnson et al. (1986), supra. The primary modification is the replacement of the forward light scatter diode detector with a forward fluorescence detector, necessary for orienting and sorting intact and viable sperm. The modification allows the collection of fluorescence from the brighter edge of the sperm (existing 90° fluorescent detector, which selects the proportion of sperm orientated properly) as well as the dimmer face of the sperm whose fluorescence is collected by the forward detector only from orientated sperm. The standard EPICS® uses a 76 $\mu$m conical flow nozzle which was replaced by the elliptical nozzle of the invention having the measurements indicated in Table I. The MoFlo® high speed system was adapted with a complete flow cell system common to the EPICS® system and was then able to receive the elliptical nozzle. Sperm intersected the laser beam after passing through the stream jet-in-air nozzle. The nozzle alone is responsible for orienting the sperm and can do so with either the standard cylindrical needle or with a beveled needle. The fluorochrome of the stained sperm was excited with ultraviolet light.

To fully demonstrate the efficacy of this invention, several experiments were conducted. The first 5 experiments (Examples 1–5) outlined below were designed to quantify (Student's t-test for small samples) the improvement in orientation and sorting obtained by the nozzle of the invention. The last two experiments (Examples 6 & 7) applied the nozzle of the invention to the high efficiency sorting of X and Y sperm for fertilization which would otherwise not have been possible.

When purities of the sorted samples are reported, the percentages were determined by the flow cytometric reanalysis of the sorted sample. Aliquots (100,000 to 250,000 sperm) of sperm were pulse sonicated to remove tails (allowing for better precision in analysis). Sperm were then restrained and rerun on the flow cytometer. Resulting histograms were fit with a double Gaussian curve fitting routine.

Example 1

In this Example, the performance of the nozzle of the invention was compared with a standard sperm sorting system and with a system using a beveled needle with an inclusive angle of 12° at the outlet end. Semen of 8 different bulls was analyzed on two different days with the standard conical nozzle and standard cylindrical injection needle. Semen of 15 different bulls was analyzed on three different days and measured with: 1) the standard conical nozzle and beveled needle, 2) the elliptical nozzle and standard cylindrical needle.

Sample rates were about 2000 sperm per second. Window settings to select oriented sperm signals were the same for each experiment. Measurements of sperm with the standard and elliptical nozzles were done with two different cell sorters (EPICS® V and EPICS® 750). In this way, low proportions of oriented sperm caused by changing needles backwards and forwards was avoided.

A large improvement in bull sperm orientation was achieved using the elliptical nozzle compared with the standard nozzle fitted with a cylindrical or beveled needle (paired difference t-tests, p<0.05, separate data not shown). On average, a 3.0 times larger proportion of oriented sperm was obtained with the elliptical nozzle (52.5±4.7%, n=15) when compared with standard conical nozzle in combination with the standard cylindrical needle (17.3±0.7%, n=8) and a 2.3 times larger proportion of oriented sperm when compared with the standard nozzle in combination with the beveled needle (22.7±3.5%, n=15).

Example 2

This example was designed to analyze the influence of sperm motility on orientation by the elliptical nozzle of the invention. Motility is an important feature of viable sperm, as only motile sperm samples are considered suitable for sexing and fertilization. Proportions of oriented intact viable sperm were compared with proportions of oriented sperm without their tails and proportions of oriented dead intact sperm. Measurements were performed on four different days with semen of different bulls. Sample rates were about 2000 sperm per second. Viable sperm could be analyzed separately from dead sperm by their differential Hoechst fluorescence, because PI, which only stains dead sperm, quenches Hoechst fluorescence.

Proportions of oriented viable bull sperm (56.8±6.7%) were the same as those of tailless bull sperm (59.8±4.2%) or dead bull sperm (53.3±4.3%, no significant difference at p=0.05, n=4), showing that motility has a negligible influence on orientation of bull sperm when the novel elliptical nozzle is used.

Example 3

This example was designed to assess the influence of sample rate on orientation. Sample rate is important as it is advantageous to sort sperm in the shortest amount of time possible. Semen of 8 bulls was measured on two days with sample rates of 500 sperm/sec and 2000 sperm/sec. Orientations of 52.1±6.4% and 52.3% ±6.5 were obtained for sample rates of 500 sperm/sec. and 2000/sec. (n=8, paired difference t-test), respectively, demonstrating that orientation was not influenced by sample rate.

Example 4

In Example 4, sperm collected from rabbits, mice and humans were evaluated to investigate the orientation performance of the elliptical nozzle for these species with contrasting sperm morphology. Semen of 3 different rabbits was analyzed with the elliptical nozzle and proportions of correctly oriented sperm were determined. Additionally, mouse sperm and frozen-thawed human sperm were analyzed to demonstrate the use of this nozzle for these species.

A high proportion of rabbit sperm were correctly oriented when measured with the elliptical nozzle (48±2.4% n=3). The proportion of oriented sperm obtained with mouse sperm and human cryopreserved-thawed sperm was 44% and 45% respectively.

Example 5

This example was designed to test the ability of the novel nozzle system for producing sufficient numbers of sorted populations of sperm from two different species that could then be shipped by air to different regions of the country and used the same day for in vitro fertilization of oocytes at that particular location. High purity sorted samples were obtained on all days of the experiment (Table III). On average, a X-sperm sort purity of 87.6% ±3.1% and a Y-sperm sort purity of 89.3±2.5% were obtained for borine sperm.

Figure 4A:
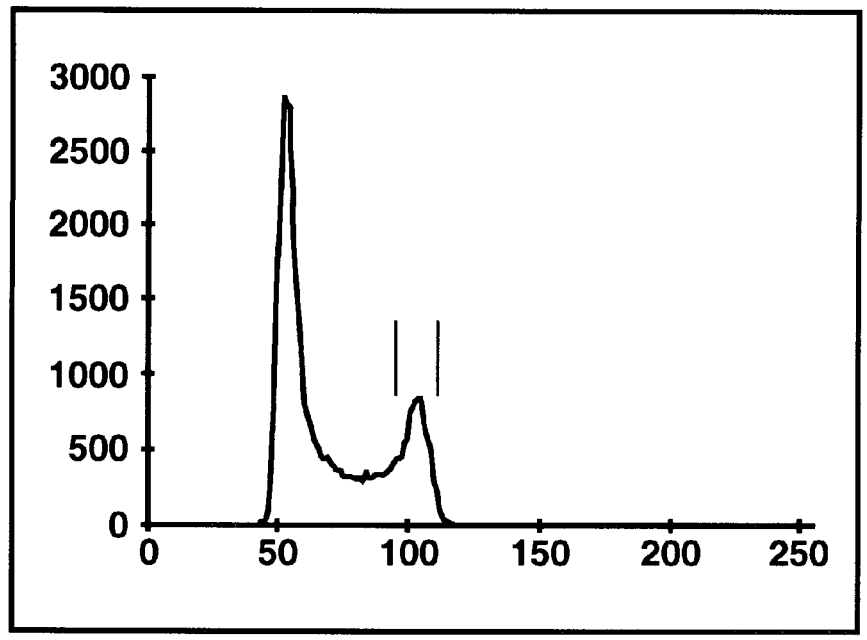
FIG. 4A is an orientation histogram of boar intact sperm measured with a beveled needle/conical nozzle system of the prior art.
Figure 4B:
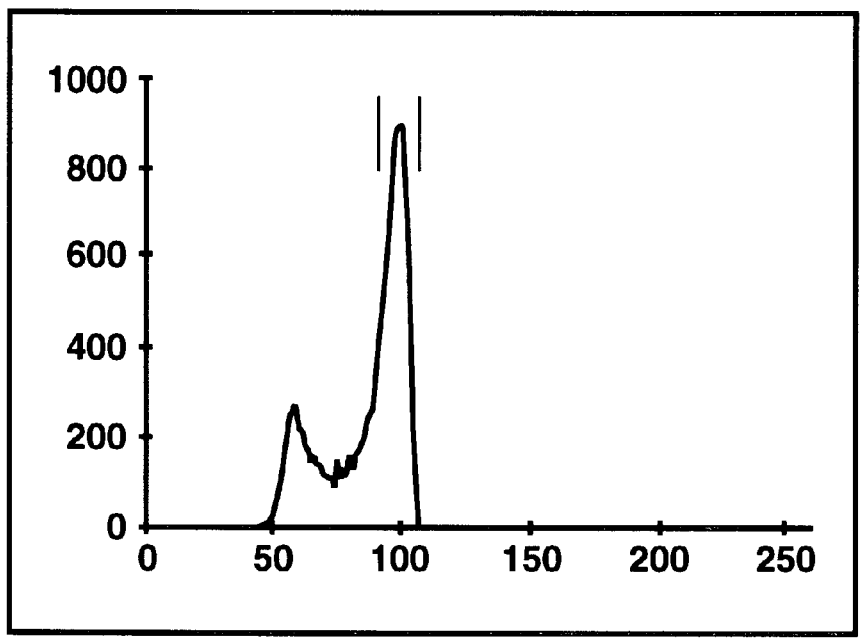
FIG. 4B is an orientation histogram of boar intact sperm measured with a conventional cylindrical needle/elliptical nozzle in accordance with the invention.

Boar sperm orientation on average was characterized by a X-sperm sort purity of 85.3±2.10% and a Y-sperm sort purity of 89.4±2.4% was obtained (Table IV). Proportions of orientated sperm were on average 60.5±0.9%. Orientation histograms obtained with the conical nozzle/beveled needle system and with the elliptical nozzle/cylindrical needle are presented in FIGS. 4A and 4B, respectively, to show the significant improvement in orientation. The paired vertical bars in the figures represent the orientation window required for effective sorting of X- and Y-chromosome bearing sperm.

Example 6

Example 6 demonstrates that sufficient sperm could be sorted in a short time, yet in sufficient magnitude to use the sorted sperm for regular artificial insemination in cattle. Two million sorted X and Y sperm using both boar and bull sperm needed to be sorted and recovered at approximately 90% purities (85–95%) between 9am and noon and 8am and 10am respectively. These constraints were imposed because of required counter to counter air shipment times which enabled same day in vitro fertilization (IVF) by Research collaborators in other states.

The sorts described above were successfully carried out 4 times for boar IVF and 6 times for bull IVF. The previous sorting technology which only allowed several hundred thousand sperm to be recovered per hour would have made these experiments impossible to do.

Example 7

Sorted X and Y (primarily X) sperm were used for artificial insemination of dairy cows. Four to five million sperm were required at approximately 90% purity (85–90%) for each recipient. Up to 5 recipients were to be artificially inseminated per day with sorted sperm. Therefore, up to 25 million×sperm (50 million, total X and Y) were required to be sorted between 9am and 4pm. This would not have been possible without the nozzle of the invention. These experiments (from 1 to 5 cows) were successfully carried out 5 times.

TABLE I

Parameters of Preferred Embodiment

|  | A | B | a | b | c | X | Y |
|---|---|---|---|---|---|---|---|
| Actual (mm) | 6 | 7 | 0.9 | 2 | 0.2 | 5.5 | 2.5 |
| Relative to c | 30c | 35c | 4.5c | 10c | — | 27.5c | 12.5c |

TABLE II

Significant Dimensional Ratios of Preferred Embodiment

| Relationship | Ratio | Minus 20% | Plus 20% |
|---|---|---|---|
| B/A | 1.2 | >1.0 | 1.4 |
| b/a | 2.2 | 1.8 | 2.6 |
| a/c | 4.5 | 3.6 | 5.4 |
| X/A | 0.9 | 0.7 | 1.1 |
| Y/a | 2.8 | 2.2 | 3.4 |
| A/a | 6.7 | 5.4 | 8 |
| B/b | 3.5 | 2.8 | 4.2 |

TABLE III

Sort purities of bovine (bull) X-sperm and Y-sperm measured with the elliptical nozzle

| Day | Orientation (%) | X-sort (%) | Y-sort (%) |
|---|---|---|---|
| 1 | 50 | 88.0 | 90.5 |
| 2 | 57 | 91.5 | 90.5 |
| 3 | 59 | 84.0 | 85.5 |
| 4 | 52 | 87.0 | 90.5 |
| Mean ± sd | 54.5 ± 4.2 | 87.6 ± 3.1 | 89.3 ± 2.5 |

TABLE IV

Sort purities of porcine (boar) X-sperm and Y-sperm measured with the elliptical nozzle

| Day | Orientation | X-sort (%) | Y-sort (%) |
|---|---|---|---|
| 1 | 61.5 | 84.0 | 89.0 |
| 2 | 60.0 | 84.3 | 87.3 |
| 3 | 60.0 | 87.7 | 92.0 |
| Mean ± sd | 60.5 ± 0.9 | 85.3 ± 2.1 | 89.4 ± 2.4 |

We claim:

1. A nozzle comprising a body having a first interior zone and a second interior zone, said first and second zones being separated by a transition zone, wherein essentially all cross-sections of said first and second zones and said transition zone are in the shape of an ellipse having a long axis and a short axis, wherein said first zone comprises a mouth and is tapered from said mouth to said transition zone such that the cross-sectional area of said transition zone is less than that of the mouth and the ratio of the long axis to the short axis increases as the cross-sectional area of the first zone decreases from the mouth to the transition zone, wherein said second zone is downwardly tapered from said transition zone to an exit orifice having a cross-sectional area less than that of the transition zone and the ratio of the lone axis to the short axis decreases from the transition zone to a point within the second zone where said lone and short axes are equal and thereafter the ratio of the long axis to short axis increases and the lone axis is at approximately 90° to the lone axis in both of said mouth and said transition zone, and wherein the long axis in said exit orifice is at approximately 90° to the long axes in both of said mouth and said transition zone.

2. The nozzle of claim 1 wherein said nozzle further comprises means for attachment to a flow cell.

3. The nozzle of claim 2 wherein said means for attachment are interior threads adjacent to said first zone and adapted to be received by exterior threads on said flow cell.

4. The nozzle of claim 2 wherein said means for attachment is a pressure fitting.

5. The nozzle of claim 1 wherein said body further comprises a cylindrical orifice downstream from, and of smaller cross-section than, said exit orifice.

6. The nozzle of claim 1 wherein dimensions A and B are the short and the long axes, respectively, of said mouth, dimensions a and b are the short and the long axes, respectively, in said transition zone, dimension a is also the long axis in said exit orifice, dimension c is the short axis in said exit orifice, dimension X is the height of said first zone and dimension Y is the height of said second zone and the ratio of B/A is in the range of about 1.1–1.4, the ratio of b/a is in the range of about 1.8–2.6, the ratio of a/c is in the range of about 3.6–5.4, the ratio of X/A is in the range of about 0.7–1.1, the ratio of Y/a is in the range of about 2.2–3.4, the ratio of A/a is in the range of about 5.4–8.0, and the ratio of B/b is in the range of about 2.8–4.2.

7. The nozzle of claim 1 wherein dimensions A and B are the short and the long axes, respectively, in said mouth, dimensions a and b are the short and the long axes, respectively, in said transition zone, dimension a is also the long axis in said exit orifice, dimension c is the short axis in said exit orifice, dimension X is the height of said first zone and dimension Y is the height of said second zone and the value of A is about 6 mm, the value of B is about 7 mm, the value of a is about 0.9 mm, the value of b is about 2 mm, the value of c is about 0.2 mm, the value of X is about 5.5 mm and the value of Y is about 2.5 mm.

* * * * *